(12) United States Patent
Bothe et al.

(10) Patent No.: US 7,250,408 B2
(45) Date of Patent: Jul. 31, 2007

(54) GLUCOCORTICOID RECEPTOR ANTAGONISTS FOR PROPHYLAXIS AND THERAPY OF GLUCOCORTICOID-MEDIATED HYPOGONADISM, OF SEXUAL DYSFUNCTION AND/OR INFERTILITY

(75) Inventors: Ulrich Bothe, Jena (DE); Gerd Schubert, Jena (DE); Guenter Kaufmann, Jena (DE); Lothar Sobek, Jena (DE); Vladimir Patchev, Jena (DE); Alexander Hillisch, Jena (DE)

(73) Assignee: Bayer Schering Pharma AG, Berlin (DE)

( * ) Notice: Subject to any disclaimer, the term of this patent is extended or adjusted under 35 U.S.C. 154(b) by 499 days.

(21) Appl. No.: 10/735,487

(22) Filed: Dec. 12, 2003

(65) Prior Publication Data

US 2004/0180869 A1 Sep. 16, 2004

Related U.S. Application Data

(60) Provisional application No. 60/443,745, filed on Jan. 30, 2003.

(30) Foreign Application Priority Data

Dec. 16, 2002 (DE) ............................ 102 59 004

(51) Int. Cl.
*A61K 31/56* (2006.01)
*C07J 1/00* (2006.01)

(52) U.S. Cl. ..................... 514/179; 552/629
(58) Field of Classification Search ............ 552/629; 514/179
See application file for complete search history.

(56) References Cited

U.S. PATENT DOCUMENTS

| 4,477,445 A | * | 10/1984 | Philibert et al. ............ 514/172 |
| 5,620,966 A | * | 4/1997 | Gebhard et al. ............ 514/174 |
| 6,072,068 A | * | 6/2000 | Groen et al. ................. 558/54 |

FOREIGN PATENT DOCUMENTS

| EP | 0 057 115 B1 | 3/1985 |
| EP | 0 683 172 A1 | 11/1995 |
| EP | 0 793 541 B1 | 9/1999 |
| WO | 95/04536 | 2/1995 |
| WO | WO 95/04536 | * 2/1995 |
| WO | 96/20795 | 7/1996 |
| WO | 01/47859 A1 | 7/2001 |

OTHER PUBLICATIONS

Moguilewsky, M. Philibert et al: "The Antiprogestin Steroid . . . " p. 87-97, Plenum Press, New York, London 1984.
Lynnette K. Nieman et al: "Successful Treatment of Cushing's Syndrome . . . ", J. Clin. Endorc. Metab. 6, vol. 1, p. 536-540, 1985.
R. Gebhard et al: "11.21-Bisphenyl-19-Norpregnane . . . ", Bioorganic & Medicinal Chemistry Letters 7, pp. 2229-2234, 1997.
Pharmabusiness 21, p. 152, 2002.

\* cited by examiner

*Primary Examiner*—Barbara P. Badio
(74) *Attorney, Agent, or Firm*—Michael J. Striker

(57) ABSTRACT

The novel glucocorticoid receptor antagonists are 11β-substituted steroid compounds of formula (I):

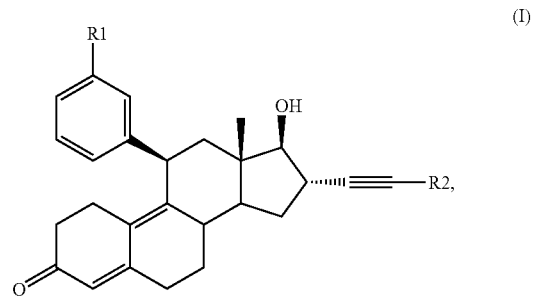

wherein $R_1$ denotes a methyl group, a methoxy group, or an ethoxy group; wherein $R_2$ denotes a tert.-butyl group, a 1-hydroxy-1-methylethyl group, a 1-methoxy-1-methylethyl group, an ethyl isocrotonate group, or a substituted phenyl group. The method of treating an individual suffering from glucocorticoid-mediated hypogonadism, sexual dysfunctions, and/or infertility includes administering a daily dosage consisting of an effective amount of one of these 11β-substituted steroid compounds.

10 Claims, No Drawings

GLUCOCORTICOID RECEPTOR ANTAGONISTS FOR PROPHYLAXIS AND THERAPY OF GLUCOCORTICOID-MEDIATED HYPOGONADISM, OF SEXUAL DYSFUNCTION AND/OR INFERTILITY

CROSS-REFERENCE

The present application claims the benefit of priority of invention based on U.S. Provisional Patent Application, Ser. No.: 60/443,745, filed Jan. 30, 2003, which, in turn, claims the benefit of priority of invention based on DE 102 59 004.4, filed Dec. 16, 2002, in Germany under 35 U.S.C. 119.

BACKGROUND OF THE INVENTION

The invention relates to new glucocorticoid receptor antagonists for producing a new drug for the prophylaxis and therapy of glucocorticoid-mediated hypogonadism, sexual dysfunctions and/or infertility.

For purposes of the present invention, by "glucocorticoid receptor antagonists" are meant pharmaceuticals capable of competitively inhibiting the action of glucocorticoids by better and more selective binding to the glucocorticoid receptors.

It is known that with advancing age and physical and/or mental stress and in the human body the corticoid level is elevated relative to the level of sex hormones and that exogenous factors such as drug abuse and alcohol abuse can lead to sexual dysfunctions and hypogonadism. These disorders occur as a result of reduced endogenous androgen production, particularly as a result of reduced production of testosterone in the testes and by a "corticoid-mediated" increase in testosterone degradation. Moreover, as a result of hypophyseal suppression, the secretion of ACTH is reduced and, secondary to that, the production of adrenal androgen is also reduced (Hatz, H. J., "Glucocorticoide" [Glucocorticoids], page 231, Wissenschaftliche Verlagsgesellschaft mbH, Stuttgart, 1998 [publisher]).

Various attempts have been made to treat the foregoing disorders. The drugs used for this purpose are only partly suitable in terms of their efficacy, selectivity and adverse reactions to which they give rise.

For example, EP 0057117 discloses as a glucocorticoid receptor antagonist the compound 11β-(4-dimethylamino) phenyl-17β-hydroxy-17α-propyn-1-yl-estra-4,9-dien-3-one, RU 38486, which binds to the progesterone receptor and glucocorticoid receptor almost equally strongly and is currently permitted for therapeutic termination of pregnancy in its early stages [Moguilewsky, M., Philibert, D., in: The Antiprogestin Steroid 11β-(4-dimethylamino)phenyl-17β-hydroxy-17α-propyn-1-yl-estra-4,9-dien-3-one (RU 38486) and Human Fertility Control, page 87, Plenum Press, New York, London, 1985, (editors: Baulieu, E. E. and Segal, S. J.)] or for the treatment of Cushing's syndrome [Nieman, L. K., Chrousos, G. P., Kellner, C. K., Spitz, I. M., Nisula, B. C., et al., J. Clin. Endocr. Metab. 61, 536 (1985)]. The use of antiglucocorticoids for the treatment of anxiety disorders is described in the application WO 95/04536 (Peeters, B.).

Gebhard, R., describes in the patents EP 0 683 172 A1 and EP 0 793 541 A1 and in Bioorganic & Medicinal Chemistry Letters 7, 2229-2234 (1997) a number of 11,21-bisphenyl-19-norpregnanes for the treatment of diseases mediated by certain glucocorticoids, such as Cushing's syndrome, diabetes, glaucoma, depression, arteriosclerosis, adiposity, high blood pressure, sleep disorders and osteoporosis.

Until now, with the exception of 11β-(4-dimethylamino) phenyl-17β-hydroxy-17α-propyn-1-yl-estra-4,9-ien-3-one (RU 38 486), a very strongly but not very selectively binding substance, no compound has been developed as an antiglucocorticoid for therapy. One compound (ORG 34 517) is currently in phase II/III clinical trials for depression as the indication [PharmaBusiness 51, 152 (2002)].

SUMMARY OF THE INVENTION

Hence an object of the present invention is to compensate for reduced androgen production and to treat or prevent the disorders caused by a relevant glucocorticoid excess.

It is also an object of the present invention to provide drugs that can be used effectively for the treatment and/or prevention of disorders which as a result of an excess of cortisol have led to reduced androgen production.

According to the invention, the foregoing objective is reached by use of glucocorticoid receptor antagonists with a relative binding affinity for the glucocorticoid—receptor bond between 85% and 155% of that of dexamethasone, and with a relative binding affinity for the progesterone—receptor bond between 1% and 11% of that of progesterone, or with a 14-fold and 150-fold dissociation between the two receptor types, for the production of a drug for the prophylaxis and therapy of glucocorticoid-mediated hypogonadism, sexual dysfunctions and/or infertility.

Moreover, the objective of preparing 11β-substituted steroids as glucocorticoid receptor antagonists of general formula I

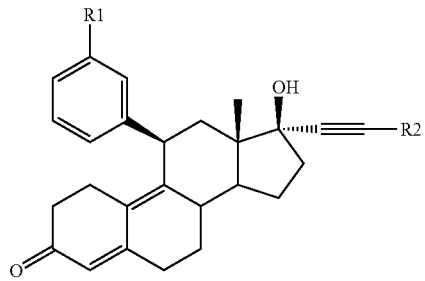

wherein $R_1$ denotes an alkyl or alkoxy group and $R_2$ a tert.butyl group, sec. propyl alcohol, sec. propyl ether or substituted benzene ring, has been attained.

Advantageously, the 11β-benzene ring is substituted in the m-position and contains no ring connection to another position. It is particularly advantageous if the m-substituent is a methyl, methoxy or ethoxy group.

Another advantageous embodiment of the invention is one in which $R_2$ is a tertiary butyl group, secondary propyl alcohol, secondary propyl ether or substituted benzene ring.

Preferred compounds for the treatment or prevention of glucocorticoid-mediated hypogonadism, sexual dysfunctions and/or infertility the special and detailed preparation of which has thus far not been described are:

21-tert.butyl-17-hydroxy-11β-(3-methoxyphenyl)-19-nor-17α-pregna-4,9-dien-20-yn-3-one,
methyl-4-{17-hydroxy-11β-[3-(methoxy)phenyl]-3-keto-19-nor-17α-pregna-4,9-dien-20-yn-21-yl)}benzoate,
3-{17-hydroxy-11β-[3-(methoxy)phenyl]-3-keto-19-nor-17α-pregna-4,9-dien-20-yn-21-yl)}benzaldehyde,
4-{17-hydroxy-11β-[3-(methoxy)phenyl]-3-keto-19-nor-17α-pregna-4,9-dien-20-yn-21-yl)}phenylacetate, 17-hydroxy-11β-[3-(methoxy)phenyl)]-21-(4-pyrrolyl)phenyl-19-nor-17α-pregna-4,9-dien-20-yn-3-one,
17-hydroxy-21-(4-hydroxyphenyl)-11β-[3-(methoxy)phenyl)]-19-nor-17α-pregna-4,9-dien-20-yn-3-one,
17-hydroxy-21-(4-mesylphenyl)-11β-(3-methoxyphenyl)-19-nor-17α-pregna-4,9-dien-20-yn-3-one,
21-tert.butyl-17-hydroxy-11β-(3-ethoxyphenyl)-19-nor-17α-pregna-4,9-dien-20-yn-3-one,
21-(4-tert.butylphenyl)-17-hydroxy-11β-(3-methoxyphenyl)-19-nor-17α-pregna-4,9-dien-20-yn-3-one,
ethyl(E)-3-[17-hydroxy-11β-(3-methoxyphenyl)-3-keto-19-nor-17α-pregna-4,9-dien-20-yn-21-yl)}isocrotonate,
21-(3,5-difluorophenyl)-17-hydroxy-11β-(3-methoxyphenyl)-19-nor-17α-pregna-4,9-dien-20-yn-3-one,
21-(2-trifluorophenyl)-17-hydroxy-11β-(3-methoxyphenyl)-19-nor-17α-pregna-4,9-dien-20-yn-3-one,
21-(3,5-dimethylphenyl)-17-hydroxy-11β-(3-methoxyphenyl)-19-nor-17α-pregna-4,9-dien-20-yn-3-one,
4-{17-hydroxy-11β-[3-(methoxy)phenyl]-3-keto-19-nor-17α-pregna-4,9-dien-20-yn-21-yl)}phenylsulfamate,
17-hydroxy-21-(1-hydroxy-1-methylethyl)-11β-(3-methoxyphenyl)-19-nor-17α-pregna-4,9-dien-20-yn-3-one,
3-(17-hydroxy-3-keto-19-nor-17α-pregna-4,9-dien-20-yn-11β-yl)benzaldehyde,
(E)-3-[17-hydroxy-11β-(3-methoxyphenyl)-3-keto-19-nor-17α-pregna-4,9-dien-20-yn-21-yl)benzaldoxime,
17-hydroxy-21-(1-methoxy-1-methylethyl)-11β-(3-methoxyphenyl)-19-nor-17α-pregna-4,9-dien-20-yn-3-one,
17-hydroxy-21-(4-mesylphenyl)-11β-(3-methylphenyl)-19-nor-17α-pregna-4,9-dien-20-yn-3-one,
17-hydroxy-21-(4-mesyloxyphenyl)-11β-(3-methylphenyl)-19-nor-17α-pregna-4,9-dien-20-yn-3-one, and
4-{17-hydroxy-11β-[3-methylphenyl)]-3-keto-19-nor-17α-pregna-4,9-dien-20-yn-21-yl)}phenylaminoacetate.

Another advantageous embodiment of the invention involves the use of 11β-substituted steroids as glucocorticoid receptor antagonists in the preparation of a drug for the prophylaxis and therapy of glucocorticoid-mediated hypogonadism, sexual dysfunctions and/or infertility.

The glucocorticoid antagonists can be tested for efficacy, for example, by incubating a test compound together with a glucocorticoid in a test system for glucocorticoid receptors and determining whether in this test system the glucocorticoid-mediated action is reduced in the presence of the antagonist. It can be confirmed on Leydig cells that the glucocorticoid-mediated suppression of testosterone biosynthesis can be reduced or completely abolished by glucocorticoid antagonists.

The present invention is based on the finding that upon administration of special glucocorticoid receptor antagonists, androgen production which previously had been reduced by glucocorticoid excess has again increased and become normal. When, for example, Leydig cells (cells present in the testes and producing male sex hormones) are stimulated with human choriogonadotropin (hCG), the testosterone production by these cells increases. If the cells are incubated with hCG and a very strong glucocorticoid, for example dexamethasone, a significant reduction in testosterone production can be observed. We have now found that the reduction in testosterone production by the glucocorticoid dexamethasone in such an experiment can be counteracted if dexamethasone is administered together with a glucocorticoid receptor antagonist. This effect can be observed not only in isolated Leydig cells but also in test animals.

In test subjects, age-mediated or stress-mediated elevated glucocorticoid blood levels cause inhibition of endocrine secretory activity of human gonads as indicated by the lowering of the serum testosterone level. Inhibition (reduction) of male sexual activity is observed at the same time. These symptoms, among others, are characteristic of hypogonadism, but are also observed for other clinical conditions, for example stress and particularly chronic stress.

The new glucocorticoid receptor antagonists bind selectively to the glucocorticoid receptor thus displacing from the receptor the natural (endogenous) ligands of the glucocorticoid receptors, i.e., the glucocorticoids, without themselves eliciting a glucocorticoid effect. Selective antagonization of the glucocorticoid receptor takes place which reduces or largely prevents signal transmission by this receptor.

This reduction or prevention of the binding to the glucocorticoid receptors by glucocorticoid receptor antagonists makes sense particularly in case of an elevated glucocorticoid level. Such an elevated glucocorticoid level can be caused, for example, by (1) aging, (2) pathological elevation of the secretory activity of the adrenal glands, (3) physical or mental stress and (4) alcohol abuse and drug abuse and withdrawal.

Data concerning the angtiglucocorticoid action of the compounds of the invention or used according to the invention and based on the measurement of glucocorticoid receptor binding and progesterone receptor binding are shown in Table 1. For comparison with the systems of the invention, Table 1 also shows data for 11β-(4-dimethylamino)phenyl-17β-hydroxy-17α-propyn-1-yl-estra-4,9-dien-3-one (RU 38486), dexamethasone and progesterone, marked with an (x).

TABLE 1

Binding of Selected Compounds to the Progesterone Receptor and to the Glucocorticoid Receptor—Relative Binding Affinities (RBA Values) in %

| Example | Relative Binding Affinity to Progesterone Receptor, % | Relative Binding Affinity to Glucocorticoid Receptor, % |
|---|---|---|
| Progesterone (x) | 100 | |
| Dexamethasone (x) | | 100 |
| Example 1 | 3.4 | 85 |
| Example 3 | 4.3 | 159 |
| Example 4 | 2.8 | 98 |
| Example 5 | 3.4 | 57 |
| Example 6 | 2.9 | 109 |
| Example 7 | 1.0 | 155 |
| Example 10 | 10.4 | 148 |
| RU 38486 (x) | 504 | 683 |

As can be seen from Table 1, the compounds of the invention or used according to the invention are significantly better dissociated, meaning that they bind well to the glucocorticoid receptor and act on the progesterone receptor only slightly compared to 11β-(4-dimethylamino)phenyl-17β-hydroxy-17α-propyn-1-yl-estra-4,9-dien-3-one (RU 38486), a very active but not very selective substance. Hence, they can potentially be used for the treatment of glucocorticoid-mediated hypogonadism, sexual dysfunction or infertility.

The glucocorticoid receptor antagonists used according to the invention bind significantly more weakly to other steroid receptors. By significantly more weakly is meant that the binding to other steroid receptors elicits practically no effect.

Examples of other steroid receptors are the mineral corticoid receptors, estrogen receptors, progesterone receptors and androgen receptors. As a result of this high selectivity of the glucocorticoid receptor antagonists of the invention, because of the interaction with other nuclear receptors, the desired effects are especially highly pronounced compared to the side effects.

For use according to the invention, the glucocorticoid receptor antagonists can be administered enterally or parenterally, the human dose being, in particular, 0.01-100 mg per kg of body weight. The glucocorticoid receptor antagonist can be administered together with pharmaceutically appropriate auxiliary substances. The glucocorticoid receptor antagonist can be compressed into a solid dose unit, for example a tablet, or it can be formulated in some other manner, for example as capsules or suppositories.

By use of pharmaceutically compatible liquids, the glucocorticoid receptor antagonists can also be formulated in the form of solutions, suspensions, emulsions, preparations for injection, drops, sprays, plasters or as inhalable preparations. Moreover, medications for use according to the invention can contain additives such as fillers, dyes and polymeric binders. Basically any pharmaceutically compatible additive can be used, provided it does not negatively interfere with the function of the glucocorticoid receptor antagonist used according to the invention. Suitable carriers with which the glucocorticoid receptor antagonist can be administered include lactose, starch, cellulose derivatives and mixtures thereof.

The following examples explain the preparation and the physical properties of the special antiglucocorticoids for the treatment or prevention of glucocorticoid-mediated hypogonadism.

EXAMPLES

Example 1

21-tert.Butyl-17-hydroxy-11β-(3-methoxyphenyl)-19-nor-17α-pregna-4,9-dien-20-yn-3-one Step A n-Butyllithium (22 mL, 1.6 M in hexane) was added at −78° C. to 3,3-dimethyl-1-butyne (5 g, 61 mmol) in tetrahydrofuran [THF] (abs.), and the mixture was stirred at −78° C. for 30 minutes. Then, 3,3-dimethoxy-estra-5(10),9(11)-dien-17-one (2,5 g, 7.9 mmol) was added, and the mixture was stirred at −78° C. for 15 min and then allowed to come to room temperature (RT) overnight. Aqueous $NH_4Cl$ solution (10%, 110 mL) was added, and the resulting mixture was extracted with EtOAc (2×100 mL). The combined organic phases were washed with water (50 mL) and sodium chloride solution and then dried over sodium sulfate. Evaporation under vacuum gave a white foam which was dissolved in dichloromethane (50 mL). After addition of pyridine (0.6 mL), hexafluoroacetone sesquihydrate (0.7 mL) and aqueous hydrogen peroxide solution (50%, 6 mL) the mixture was stirred at RT for 5.5 hours. Then, aqueous $NaHCO_3$ solution (5%, 100 mL) was added, and the organic phase was separated and then washed with $NaHCO_3$ solution (5%), saturated aqueous sodium sulfite solution, water and sodium chloride solution. Drying over sodium sulfate and evaporation under vacuum gave as a crude product (3.47 g, white foam) 21-tert.butyl-3,3-dimethoxy-5,10-epoxy-19-nor-17α-pregn-(9(11)-ene-20-yn-17-ol (as 5,10-α,β diastereoisomer mixture).

$^1$H-NMR (ppm, $CDCl_3$, 400 MHz: 5.82-5.84 (m, 0.2H, 11-H, 5β,10β-epoxy compound); 6.05-6.06 (m, 0.8H, 11-H, 5α, 10α-epoxy compound).

Step B

Dibromomethane (0.1 mL) was added to magnesium (369 mg) in THF (abs., 10 mL), the mixture was stirred to incipient warming and then 3-bromoanisole (1.8 mL) in THF (18 mL) was added dropwise within 5 min at a temperature of 25-35° C. The mixture was then stirred 45 min at RT, cooled to −35° C. and then copper(I) chloride (77 mg) was added. After 7 min, the diastereoisomer mixture (1.24 g) from step A, dissolved in THF (10 mL), was added dropwise within 10 min, and the mixture was stirred 30 min at −35° C. and then 3 h at RT. Aqueous $NH_4Cl$ solution (5%, 20 mL) was added dropwise and the mixture was extracted with EtOAc. The organic phase was washed with aqueous $NH_4Cl$ solution (5%), water and aqueous sodium chloride solution. After drying over sodium sulfate and evaporation under vacuum, the mixture was purified by column chromatography on silica gel. This gave a white foam of 21-tert.butyl-3,3-dimethoxy-11β-(3-methoxyphenyl)-19-nor-17α-pregn-9-en-20-yn-5α,17-diol as a crude product (885 mg).

Step C 21-tert.Butyl-3,3-dimethoxy-11β-(3-methoxyphenyl)-19-nor-17α-pregn-9-en-20-yn-5α,17-diol (885 mg) was dissolved in acetone (30 mL). After adding p-toluenesulfonic acid monohydrate (39 mg), the mixture was stirred 1 h at RT. It was then diluted with $Et_2O$, washed twice with saturated aqueous $NaHCO_3$ solution and sodium chloride solution, dried over sodium sulfate and evaporated under vacuum, and the crude product was purified by column chromatography on silica gel. The main product was crystallized twice from acetone/cyclohexane. This gave 21-tert.butyl-17-hydroxy-11β-(3-methoxyphenyl)-19-nor-17α-pregna-4,9-dien-20-yn-3-one (468 mg) as a white solid.

$^1$H-NMR (ppm, $CDCl_3$, 400 MHz): 0.54 (s, 3H, 18-H), 1.24 (s, 9H, tert.butyl), 3.78 (s, 3H, OMe), 4.39 (d, J=6.6 Hz, 1H, 11α-H), 5.77 (s, 1H, 4-H), 6.68-6.79 (m, 3H, arom. CH), 7.18 (t, 1H, 7.8 Hz, arom CH);

LC-MS: m/z=459 [M+H$^+$].

Example 2

Methyl-4-{17-hydroxy-11β-[3-(methoxy)phenyl]-3-keto-19-nor-17α-pregna-4,9-dien-20-yn-21-yl)}benzoate Step A A solution of ethinylmagnesium bromide (948 mL, 0.5 M, 474 mmol) was added at −60° C. at a steady rate to 3,3-dimethoxy-estra-5(10),9(11)-dien-17-one (20 g, 63 mmol) in absolute THF (600 mL), and the mixture was stirred 1 h at −60° C. and then 4 h at RT. Aqueous $NH_4Cl$ solution (10%, 500 mL) was added dropwise, the organic phase was separated, the aqueous phase was extracted with EtOAc (twice with 200 mL), and the combined organic phases were washed twice with aqueous $NH_4Cl$ solution (10%). Drying over sodium sulfate gave 29.7 g of 3,3-dimethoxy-19-nor-17α-pregna-5(10),9(11)-dien-20-yn-17-ol as a crude product.

Step B

As described in Example 1, the crude 3,3-dimethoxy-19-nor-17α-pregna-5(10),9(11)-dien-20-yn-17-ol was epoxidized in dichloromethane (100 mL) with pyridine (1.4 mL), hexafluoroacetone sesquihydrate (1.25 mL) and aqueous hydrogen peroxide solution (50%, 12.5 mL). After workup, 3,3 dimethoxy-5,10-epoxy-19-nor-17α-pregn-9(11)-en-20-yn-17-ol was obtained as a yellow residue (12.6 g).

Step C

As described in Example 1, 3,3-dimethoxy-5,10-epoxy-19-nor-17α-pregn-9(11)-en-20-yn-17-ol was reacted with 3-anisolemagnesium bromide and copper(I) chloride in THF. After purification by column chromatography on silica gel (n-hexane/EtOAc 3:1), the product was crystallized from EtOAc/butyl methyl ether. This gave 3,3-dimethoxy-11β-(3-methoxyphenyl)-19-nor-17α-pregn-9-en-20-yn-5α,17 diol (3.4 g) as a white solid.

M.p.: 202 to 203° C.
$\alpha_D$=−49° (CHCl$_3$)
$^1$H-NMR (ppm, CDCl$_3$, 400 MHz): 0.56 (s, 3H, 18-H), 2.63 (s, 1H, C≡CH), 3.49 (s, 6H, 2× OCH$_3$), 3.78 (s, 3H, PhOMe), 4.41 (d, 1H J=6.8 Hz, 11α-H), 6.68-6.80 (m, 3H, arom. CH), 7.19 (t, 1H, 8.0 Hz, arom. CH).
LC-MS: m/z=467 [M+H$^+$].

Step D

As in Example 1, 3,3-dimethoxy-11β-(3-methoxyphenyl)-19-nor-17α-pregn-9-en-20-yn-5α,17 diol (2.8 g) was reacted with p-toluenesulfonic acid monohydrate in acetone. This gave 17-hydroxy-11β-(3-methoxyphenyl)-19-nor-17α-pregna-4,9-dien-20-yn-3-one (1.9 g) as a white solid.

M.p.: 131 to 133° C. (acetone).
$\alpha_D$=67° (CHCl$_3$)
$^1$H-NMR (ppm, CDCl$_3$, 400 MHz): 0.56 (s, 3H, 18-H), 2.63 (s, 1H, C≡CH), 3.78 (s, 3H, OMe). 4.41 (d, 1H, J=6.8 Hz, 11α-H), 5.76 (s, 1H, 4-H), 6.68-6.79 (m, 3H, arom. CH), 7.19 (t, 1H, 8.0 Hz, arom. CH);
LC-MS: m/z=403 [M+H$^+$].

Step E

To a solution of THF (1 mL) and triethylamine (5 mL) were added one after another under inert gas and with stirring palladium acetate (11 mg) and triphenylphosphine (20 mg) and then, after 10 min, copper(I) iodide (21 mg). After an additional 20 min, methyl 4-iodobenzoate (300 mg) and 17-hydroxy-11β-(3-methoxyphenyl)-19-nor-17α-pregna-4,9-dien-20-yn-3-one (425 mg, 1.06 mmol) were added. The mixture was stirred 2 h at +50° C. After cooling to RT, saturated aqueous NH$_4$Cl solution (20 mL) and EtOAc (20 mL) were added. The organic phase was separated, and the aqueous phase was extracted with EtOAc. The combined organic phases were washed twice with saturated aqueous NH$_4$Cl solution, water and sodium chloride solution. After drying over sodium sulfate, the mixture was evaporated under vacuum and purified by column chromatography on silica gal. Crystallization from toluene/Et$_2$O gave a white solid (395 mg).

Melting point: 120-123° C. (toluene/Et$_2$O).
$^1$H-NMR (ppm, CDCl$_3$, 400 MHz): 0.62 (3H, 18-H) [sic], 3.79 (s, 3H, OMe), 3.92 (s, 3H, COOMe), 4.43 (d, 1H, J=5.8 Hz, 11α-H), 5.76 (s, 1H, 4-H), 6.68-6.80 (m, 3H, arom. CH), 7.20 (t, 1H, 8.2 Hz, arom. CH), 7.49-7.52 (m, 2H, arom. CH), 7.97-8.00 (m, 2H, arom. CH);
LC-MS: m/z=537 [M+H$^+$].

Example 3

3-{17-Hydroxy-11β-[3-(methoxy)phenyl]-3-keto-19-nor-17α-pregna-4,9-dien-20-yn-21-yl}benzaldehyde As in Example 2, step E, 17-hydroxy-11β-(3-methoxyphenyl)-19-nor-17α-pregna-4,9-dien-20-3-one (120 mg, 0.30 mmol) was reacted with 3-bromobenzaldehyde under an argon atmosphere in an ultrasonic bath at RT by the method of Sonagashira. Purification by column chromatography on silica gel gave a slightly yellowish foam (85 mg).

$^1$H-NMR (see Example 2): 0.62 (3H, 18-H) [sic], 3.79 (s, 3H, OMe), 4.43 (d, 1H, 11α-H), 5.76 (s, 1H, 4-H), 6.7-6.8 (m, 3H, arom. CH), 7.2 (m, 1H, arom. CH), 7.51-7.53 (m, 1H, arom. CH), 7.69-7.71 (m, 1H, arom. CH), 7.82-7.83 (m, 1H, arom. CH), 7.96-7.97 (m, 1H, arom. CH), 10.0 (s, 1H, —CHO).
LC-MS: m/z=507 [M+H$^+$].

Example 4

4-{17-Hydroxy-11β-[3-(methoxy)phenyl)]-3-keto-19-nor-17α-pregna-4,9-dien-2-yn-21-yl)}phenylacetate As in Example 2/step E, 17-hydroxy-11β-(3-methoxyphenyl)-19-nor-17α-pregna-4,9-dien-20-yn-3-one (403 mg, 1.0 mmol) was made to react with 4-iodophenyl acetate (273 mg, 1.04 mmol), palladium acetate (11 mg), triphenylphosphine (26 mg) and copper(I) iodide (19 mg) in THF (abs., 10 mL) and triethylamine (10 mL) within 45 min at RT. After workup and purification by column chromatography on silica gel, a white solid (373 mg) was obtained.

$^1$H-NMR (see Example 2): 0.61 (3H, 18-H) [sic], 2.30 (s, 3H, OAc), 3.79 (s, 3H, OMe), 4.41 (d, J=6.6 Hz, 1H, 11α-H), 5.76 (s, 1H, 4-H), 6.69-6.80 (m, 3, arom. CH), 7.04-7.07 (m, 2H, arom. CH), 7.20 (t, J=7.8 Hz, 1H, arom. CH), 7.44-7.47 (m, 2H arom. CH).
LC-MS: m/z=537 [M+H$^+$].

Example 5

17-Hydroxy-11β-[3-(methoxy)phenyl)]-21-(4-pyrrolyl)phenyl-19-nor-17α-pregna-4,9-dien-20-yn-3-one As in Example 2/step E, 17-hydroxy-11β-(3-methoxyphenyl)-19-nor-17α-pregna-4,9-dien-20-yn-3-one (300 mg, 0.75 mmol) was made to react with 4-iodophenylpyrrole (261 mg, 0.97 mmol), palladium acetate (17 mg), triphenylphosphine (39 mg) and copper(I) iodide (28 mg) in THF (abs., 2 mL) and triethylamine (8 mL) within 60 min at RT in an ultrasonic bath. After workup and purification by column chromatography, a white solid was obtained (338 mg).

$^1$H-NMR (CDCl$_3$, selected data): 0.62 (3H, 18-H) [sic], 3.79 (s, 3H, OMe), 4.43 (d, 1H, 11α-H), 5.76 (s, 1H, 4-H), 6.35-6.36 (m, 2H, arom. CH), 6.69-6.81 (m, 3H, arom. CH), 7.2 (m, 1H, arom. CH), 7.15-7.16 (m, 2H, arom. CH), 7.2 (m, 1H, arom. CH), 7.33-7.36 (m, 2H, arom. CH), 7.49-7.51 (m, 2H, arom. CH).
LC-MS: m/z=544 [M+H$^+$].

Example 6

17-Hydroxy-21-(4-hydroxyphenyl)-11β-[3-(methoxy)phenyl)]-19-nor-17α-pregna-4,9-dien-20-yn-3-one A solution of 4-{17-hydroxy-11β-[3-(methoxy)phenyl]-3-keto-19-nor-17α-pregna-4,9-dien-20-yn-21-yl}phenylacetate (215 mg, 0.4 mmol) and sodium hydrogen carbonate (312 mg, 3.7 mmol) in methanol (15 mL) was stirred at RT until the reaction was complete. After the usual workup, the crude product was purified by chromatography on silica gel and crystallization from methanol.

(Yield: 114 mg).
Melting point: 213-214° C.

$^1$H-NMR (see Example 2): 0.60 (3H, 18-H) [sic], 3.79 (s, 3H, OMe), 4.39 (d, J=6.6 Hz, 1H, 11α-H), 5.79 (s, 1H, 4-H), 6.69-6.80 (m, 5H, arom. CH), 7.08 (s, 1H, arom. C—OH, 7.20 (t, J=7.8 Hz, 1H, arom. CH), 7.29-7.31 (m, 2H arom. CH).
LC-MS: m/z=495 [M+H$^+$].

Example 7

17-Hydroxy-21-(4-mesylphenyl)-11,6-(3-methoxyphenyl)-19-nor-17α-pregna-4,9-dien-20-yn-3-one As in Example 2 (step E), 17-hydroxy-11β-(3-methoxyphenyl)-19-nor-17α-pregna-4,9-dien-20yn-3-one (550 mg) was made to react with 4-bromophenyl methyl sulfone by the method of Sonagashira, and the crude product was purified by chromatography.

This gave 225 mg of 17-hydroxy-21-(4-mesylphenyl)-11β-(3-methoxyphenyl)-19-nor-17α-pregna-4,9-dien-20-yn-3-one as an amorphous product.
$α_D$=−48° (CHCl$_3$)
$^1$H-NMR (see Example 2): 0.62 (s, 3H, 18-H), 2.43 (s, 1H, OH), 3.05 (s, 3H, SCH$_3$), 3.79 (s, 3H, OCH$_3$), 4.43 (d, 1H, J=4.0 Hz, 11α-H), 5.76 (s, 1H, 4-H), 6.70-6.79 (m, 3H, arom. CH), 7.21 (t, 1H, 8.0 Hz, arom. CH), 7.62 and 7.89 (2d, 2H each, arom. CH).
LC-MS: m/z=557 [N+H$^+$].

Example 8

17-Hydroxy-21-(4-mesylphenyl)-1,6-(3-methylphenyl)-19-nor-17α-pregna-4,9-dien-20-yn-3-one As in Example 2 (step E), 17-hydroxy-11β-(3-methylphenyl)-19-nor-17α-pregna-4,9-dien-20-yn-3-one (837 mg) was made to react with 4-bromophenyl methyl sulfone by the method of Sonagashira, and the crude product was purified by chromatography.

This gave 283 mg of 17-hydroxy-21-(4-mesylphenyl)-11β-(3-methylphenyl)-19-nor-17α-pregna-4,9-dien-20-yn-3-one as an amorphous product.
$α_D$=−55° (CHCl$_3$)
$^1$H-NMR (see Example 2): 0.60 (s, 3H, 18-H), 2.33 (s, 3H, PhCH$_3$), 2.43 (s, 1H, OH), 3.05 (s, 3H, SCH$_3$), 4.42 (broad s, 1H, 11α-H), 5.77 (s, 1H, 4-H), 6.93-7.17 (m, 3H, arom. CH), 7.63 and 7.89 (2d, 2H each, arom. CH).
LC-MS: m/z=540 [M+H$^+$].

Example 9

17-Hydroxy-21-(4-mesyloxyphenyl)-11β-(3-methylphenyl)-19-nor-17α-pregna-4,9-dien-20-yn-3-one As in Example 2 (step E), 17-hydroxy-11β-(3-methylphenyl)-19-nor-17α-pregna-4,9-dien-20-yn-3-one (128 mg) was made to react with 4-bromophenol mesylate by the method of Sonagashira, and the crude product was purified by preparative layer chromatography.

This gave 73 mg of 17-hydroxy-21-(4-mesyloxyphenyl)-11β-(3-methylphenyl)-19-nor-17α-pregna-4,9-dien-3-one as an amorphous product.
$α_D$=−35° (CHCl$_3$).
$^1$H-NMR (see Example 2): 0.59 (s, 3H, 18-H), 2.32 (s, 3H, PhCH$_3$), 3.16 (s, 3H, SCH$_3$), 4.42 (d, 1H, J=4.8 Hz, 11α-H), 5.77 (s, 1H, 4-H), 6.94-7.17 (m, 3H, arom. CH), 7.25 and 7.49 (2d, 2H each, arom. CH).
LC-MS: m/z=556 [M+H$^+$].

Example 10

3-E-[17-Hydroxy-11β-[3-(methoxy)phenyl]-19-nor-3-keto-17α-pregna-4,9-dien-20-yn-21-yl]benzaldoxime 3-{17-Hydroxy-11β-[3-(methoxy)phenyl]-3-keto-19-nor-17α-pregna-4,9-dien-20-yn-21-yl}benzaldehyde (200 mg) in pyridine (5 mL) was stirred with hydroxylamine hydrochloride (24.7 mg) for 50 min at RT. The mixture was then poured into ice water, extracted with ethyl acetate, dried over sodium sulfate and purified on silica gel. Crystallization from diethyl ether gave a solid product (103 mg).
Melting point: 224-226° C. (diethyl ether)
$^1$H-NMR (see Example 2): 0.62 (s, 3H, 18-H), 3.79 (s, 3H, OMe), 4.43 (d, 1H, J=4.8 Hz, 11α-H), 5.78 (s, 1H, 4-H), 6.93-6.81 (m, 3H, arom. CH), 7.18-7.49 (m, 4H, arom. CH), 7.58 (s, 1H), 7.68-7.69 (m, 1H), 8.09 (s, 1H, N=OH).
LC-MS: m/z=522 [M+H$^+$].

Example 11

4-{17-Hydroxy-11β-[3-(methoxy)phenyl]-3-keto-19-nor-17α-pregna-4,9-dien-20-yn-21-yl}phenylsulfamate A solution of 17-hydroxy-21-(4-hydroxyphenyl)-11β-[3-(methoxy)phenyl]-19-nor-17α-pregna-4,9-dien-20-yn-3-one (200 mg) in dichloromethane (4 mL) was stirred with 2,6-ditert.butylpyridine (0.45 mL) and sulfamoyl chloride (285 mg) at RT under argon for 4 hours until the reaction was complete. After aqueous workup and purification on silica gel, a white foam was obtained (102 mg).
$^1$H-NMR (see Example 2): 0.61 (s, 3H, 18-H), 3.79 (s, 3H, OMe), 4.41 (d, 1H, J=5.5 Hz, 11α-H), 5.02 (br. s, 2H, NH$_2$), 5.76 (s, 1H, 4-H), 6.69-6.80 (m, 3H, arom. CH), 7.18-7.50 (m, 5H, arom. CH).
LC-MS: m/z=572 [M+H$^+$].

The invention claimed is:
1. An 11β-substituted steroid of formula (I):

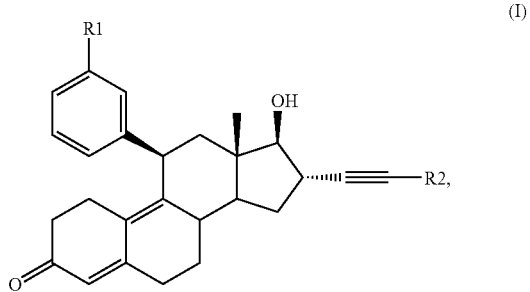

wherein R$_1$ denotes a methyl group, a methoxy group, or an ethoxy group;
wherein R$_2$ denotes a tert.butyl group, a 1-hydroxy-1-methylethyl group, a 1-methoxy-1-methylethyl group, an ethyl isocrotonate group, or a substituted phenyl group; and
wherein said substituted phenyl group has at least one substituent selected from the group consisting of methyl, hydroxy, fluoro, t-butyl, —CHO, —CH$_2$COOH, —CH=NOH, —COOCH$_3$, sulfamate, aminoacetate, mesyl, mesyloxy, and pyrrolyl.

2. The 11β-substituted steroids selected from the group consisting of
- 21-tert.butyl-17-hydroxy-11β-(3-methoxyphenyl)-19-nor-17α-pregna-4,9-dien-20-yn-3-one;
- methyl-4-{17-hydroxy-11β-[3-(methoxy)phenyl]-3-keto-19-nor-17α-pregna-4,9-dien-20-yn-21-yl)}benzoate;
- 3-{17-hydroxy-11β-[3-(methoxy)phenyl]-3-keto-19-nor-17α-pregna-4,9-dien-20-yn-21-yl)}-benzaldehyde;
- 4-{17-hydroxy-11β-[3-(methoxy)phenyl]-3-keto-19-nor-17α-pregna-4,9-dien-20-yn-21 -yI)}-phenylacetate;
- 17-hydroxy-11β-[3-(methoxy)phenyl)]-21-(4-pyrrolyl)phenyl-19-nor-17α-pregna-4,9-dien-20-yn-3-one;
- 17-hydroxy-21-(4-hydroxyphenyl)-11β-[3-(methoxy)phenyl)]-19-nor-17α-pregna-4,9-dien-20-yn-3-one;
- 17-hydroxy-21-(4-mesylphenyl)-11β-(3-methoxyphenyl)-19-nor-17α-pregna-4,9-dien-20-yn-3-one;
- 21-tert.butyl-17-hydroxy-11β-(3-ethoxyphenyl)-19-nor-17α-pregna-4,9-dien-20-yn-3-one;
- 21-(4-tert.butylphenyl)-17-hydroxy-11β-(3-methoxyphenyl)-19-nor-17α-pregna-4,9-dien-20-yn-3-one;
- ethyl(E)-3-[17-hydroxy-11β-(3-methoxyphenyl)-3-keto-19-nor-17α-pregna-4,9-dien-20-yn-21-yl)}-isocrotonate;
- 21-(3,5-difluorophenyl)-17-hydroxy-11β-(3-methoxyphenyl)-19-nor-17α-pregna-4,9-dien-20-yn-3-one;
- 21-(2-trifluorophenyl)-17-hydroxy-11β-(3-methoxyphenyl)-19-nor-17α-pregna-4,9-dien-20-yn-3-one;
- 21-(3,5-dimethylphenyl)-17-hydroxy-11β-(3-methoxyphenyl)-19-nor-17α-pregna-4,9-dien-20-yn-3-one;
- 4-{17-hydroxy-11β-[3-(methoxy)pheny]-3-keto-19-nor-17α-pregna-4,9-dien-20-yn-21-yl)}-phenylsulfamate;
- 17-hydroxy-21-(1-hydroxy-1-methylethyl)-11β-(3-methoxyphenyl)-19-nor-17α-pregna-4,9-dien-20-yn-3-one;
- 3-(17-hydroxy-3-keto-19-nor-17α-pregna-4,9-dien-20-yn-11β-yl)benzaldehyde, (E)-3-[17-hydroxy-11β-(3-methoxyphenyl)-3-keto-19-nor-17α-pregna-4,9-dien-20-yn-21-yl)]-benzaldoxime;
- 17-hydroxy-21-(1-methoxy-1-methylethyl)-11β-(3-methoxyphenyl)-19-nor-17α-pregna-4,9-dien-20-yn-3-one;
- 17-hydroxy-21-(4-mesylphenyl)-11β-(3-methylphenyl)-19-nor-17α-pregna-4,9-dien-20-yn-3-one;
- 17-hydroxy-21-(4-mesyloxyphenyl)-11β-(3-methylphenyl)-19-nor-17α-pregna-4,9-dien-20-yn-3-one; and
- 4-{17-hydroxy-11β-[3-methylphenyl]-3-keto-19-nor-17α-pregna-4,9-dien-20-yn-21 -yl}-phenylaminoacetate.

3. The 11β-substituted steroid as defined in claim 1, selected from the group consisting of
- 17-hydroxy-21-(4-hydroxyphenyl)-11β-[3-(methoxy)phenyl]-19-nor-17α-pregna-4,9-dien-20-yn-3-one,
- 17-hydroxy-21-(4-mesylphenyl)-11β-[3-(methoxy)phenyl]-19-nor-17α-pregna-4,9-dien-20-yn-3-one,
- 17-hydroxy-21-(4-mesylphenyl)-11β-[3-methylphenyl]-19-nor-17α-pregna-4,9-dien-20-yn-3-one, and
- 17-hydroxy-21-(4-mesyloxyphenyl)-11β-[3-methylphenyl]-19-nor-17α-pregna-4,9-dien-20-yn-3-one.

4. The 11β-substituted steroids as defined in claim 1, wherein $R_1$ denotes said methoxy and $R_2$ denotes said substituted phenyl wherein said at least one substituent is said —CH=NOH, said pyrrolyl, said aminoacetate, said —CHO, said hydroxy, or said sulfamate.

5. A method of therapeutic treatment of an individual suffering from glucocorticoid-mediated hypogonadism, sexual dysfunctions, and/or infertility, said method comprising the step of administering to said individual a daily dosage consisting of an effective amount of a 11β-substituted steroid for treating said glucocorticoid-mediated hypogonadism, sexual dysfunctions, and/or infertility;

wherein said 11β-substituted steroid is a steroid compound of formula (I):

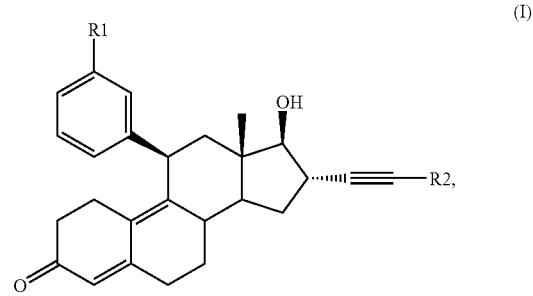

wherein $R_1$ denotes a methyl group, a methoxy group, or an ethoxy group;

wherein $R_2$ denotes a tert.butyl group, a 1-hydroxy-1-methylethyl group, a 1-methoxy-1-methylethyl group, an ethyl isocrotonate group, or a substituted phenyl group; and wherein said substituted phenyl group has at least one substituent selected from the group consisting of methyl, hydroxy, fluoro, t-butyl, —CHO, —CH$_2$COOH, —CH=NOH, —COOCH$_3$, sulfamate, aminoacetate, mesyl, mesyloxy, and pyrrolyl.

6. The method as defined in claim 5, wherein said administering of said daily dosage occurs orally, subcutaneously, sublingually, by inhaling, or topically.

7. The method as defined in claim 5, wherein said daily dosage is from 0.01 to 100 mg per kg of body weight of said individual.

8. A pharmaceutical composition for treating an individual suffering from glucocorticoid-mediated hypogonadism, sexual dysfunctions, and/or infertility, said pharmaceutical composition comprising a pharmaceutically compatible additive and an effective amount of a 11β-substituted steroid for treating said glucocorticoid-mediated hypogonadism, sexual dysfunctions, and/or infertility;

wherein said 11β-substituted steroid is a steroid compound of formula (I):

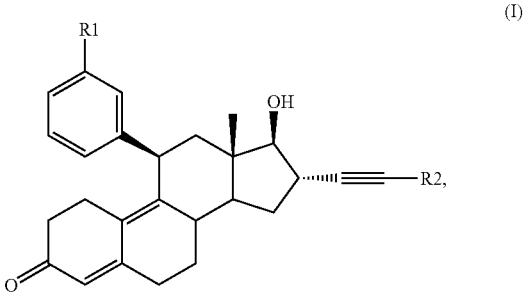

wherein $R_1$ denotes a methyl group, a methoxy group, or an ethoxy group;

wherein $R_2$ denotes a tert.butyl group, a 1-hydroxy-1-methylethyl group, a 1-methoxy-1-methylethyl group, an ethyl isocrotonate group, or a substituted phenyl group; and wherein said substituted phenyl group has at least one substituent selected from the group consisting of methyl, hydroxy, fluoro, t-butyl, —CHO, —CH$_2$COOH, —CH═NOH, —COOCH$_3$, sulfamate, aminoacetate, mesyl, mesyloxy, and pyrrolyl.

9. The pharmaceutical composition as defined in claim 8, wherein said effective amount is from 0.01 to 100 mg per kg of body weight of said individual.

10. The pharmaceutical composition as defined in claim 8, in the form of a solution, suspension, emulsion, ointment, plaster, gel, injectable preparation, inhalable preparation, a spray, or drops.

* * * * *